(12) United States Patent
Bowen et al.

(10) Patent No.: US 9,134,240 B2
(45) Date of Patent: Sep. 15, 2015

(54) SYSTEM AND METHOD FOR EVALUATING MATERIAL IN ROTARY MOTION

(75) Inventors: John Bowen, Pittsford, NY (US); Gary Blough, Ontario, NY (US)

(73) Assignee: Photon Gear, Inc., Ontario, NY (US)

( * ) Notice: Subject to any disclaimer, the term of this patent is extended or adjusted under 35 U.S.C. 154(b) by 654 days.

(21) Appl. No.: 13/553,618

(22) Filed: Jul. 19, 2012

(65) Prior Publication Data
US 2013/0020505 A1    Jan. 24, 2013

Related U.S. Application Data

(60) Provisional application No. 61/509,403, filed on Jul. 19, 2011.

(51) Int. Cl.
*F21V 9/16* (2006.01)
*G01N 21/64* (2006.01)

(52) U.S. Cl.
CPC ............ *G01N 21/6452* (2013.01); *G01N 21/64* (2013.01)

(58) Field of Classification Search
CPC ................................................ G01N 121/6452
USPC ................................... 250/458.1, 459.1, 236
See application file for complete search history.

(56) References Cited

U.S. PATENT DOCUMENTS

2003/0194219 A1*  10/2003  Cookson et al. ................. 386/95
2004/0120034 A1*   6/2004  Miyawaki et al. ............ 359/385

OTHER PUBLICATIONS

Nguyen, et al, "Surgery with molecular fluorescence imaging using activatable cell-penetrating peptides decreases residual cancer & improves survival," PNAS 107, p. 4317, 2010.
Gale, et al., "The fabrication of fine lens arrays by laser beam writing" Proc. SPIE v. 398, pp. 347-353, 1983.
Bowen, John P., et al."Generation of large-diameter diffractive elements with laser pattern generation" Applied Optics, vol. 36:34, pp. 8970-8975, 1997.

* cited by examiner

*Primary Examiner* — David Porta
*Assistant Examiner* — Meenakshi Sahu
(74) *Attorney, Agent, or Firm* — Lathrop & Gage LLP

(57) ABSTRACT

Systems and methods evaluate material in rotary motion. Exposure duration is calculated based upon an intensity of radiation incident upon a sample area of the material and a desired radiation exposure for the material. Angular velocity for a rotational stage is calculated based upon the sample area, the calculated exposure duration, and an initial position of a linear stage. The initial position of the linear stage, the initial velocity of the linear stage, and the initial angular velocity of the rotational stage are set and a radiation generator is activated. The system then waits for time to read the next data sample based upon the calculated exposure duration and a fluorescence level of the material is determined. Angular velocity of the rotational stage and linear velocity of the linear stage are controlled based upon positional sensors to capture data from all areas of the material at the desired radiation exposure.

3 Claims, 2 Drawing Sheets

SYSTEM AND METHOD FOR EVALUATING MATERIAL IN ROTARY MOTION

RELATED APPLICATIONS

This application claims priority to U.S. patent application Ser. No. 61/509,403, filed Jul. 19, 2011, which is incorporated herein by reference.

BACKGROUND

Optical measurements are commonly used to characterize and measure materials including the biological properties of such materials. In these measurements, directed optical radiation (such as from lasers or light emitting diodes) is directed onto a sample of material. Some of the radiation changes after it strikes, or passes through, the biological material. Analysis is then performed on light (fluorescence) emitted from the sample in order to determine its properties.

Many biological materials fluoresce. Fluorescence is technically emission at one wavelength after a material absorbs light of another wavelength. The emitted wavelength is longer (lower frequency) than the absorbed light. Fluorescence properties are often used in biological measurements in order to denote the presence or absence of specific molecules. In a typical example, a sample material is illuminated by incident radiation of a particular frequency, and fluorescent light of a different frequency is detected and measured. The ratio of fluorescent light to incident radiation is typically small (e.g., one part in $10^8$ to one part in $10^{12}$). A filter is therefore used to block incident radiation (often called the pump light) reflected from the sample material to prevent saturation of the detector (e.g., camera). Since the amount fluorescent light compared to the pump light is very small, the filter must pass substantially all light at the wavelength of the expected fluorescence and also block substantially all light at the wavelength of the pump light. In certain cases, biological properties of the sample material are measured over an area of the sample, and not just at one small portion of the sample material; this complicates set-up and data measurement.

A paper titled "Surgery with molecular fluorescence imaging using activatable cell-penetrating peptides decreases residual cancer and improves survival" by Q. T. Nguyen, et al., (PNAS, 107, (2010), 4317) describes one approach to measuring fluorescence and is incorporated herein by reference. However, the approach in this paper has the disadvantage in that the camera must have very low noise, as the fluorescent light from the sample material is very weak. Further, it is difficult to amplify the signal on the sensor without introducing additional noise. Typically, fluorescent light is captured over a long period, making the process more expensive.

By way of further background, a paper titled "The fabrication of fine lens arrays by laser beam writing" by M. T. Gale and K. Knop, (Proc. SPIE v. 398, page 347) describes exemplary scanning of a two dimensional stage and is incorporated herein by reference. Another paper titled "Generation of large-diameter diffractive elements with laser pattern generation" by John P. Bowen, Robert L. Michaels, and C. Gary Blough, (Applied Optics, Vol. 36, Issue 34, pp. 8970-8975 1997) discloses application of optical radiation to a sample and is likewise incorporated herein by reference.

SUMMARY

In one embodiment, a method evaluates material in rotary motion. Exposure duration is calculated based upon an intensity of radiation incident upon a sample area of the material and a desired radiation exposure for the material. Angular velocity for a rotational stage is calculated based upon the sample area, the calculated exposure duration, and an initial position of a linear stage. The initial position of the linear stage, the initial velocity of the linear stage, and the initial angular velocity of the rotational stage are set and a radiation generator is activated to expose the sample area to radiation. The system then waits for time to read the next sample based upon the calculated exposure duration. Data is read from the detector, a fluorescence level is determined based upon the data, and the data is stored in memory. Positional sensors are read and angular velocity of the rotational stage is calculated and set and linear velocity of the linear stage is calculated and set. The method waits, reads data and positional sensors, and sets position of the linear stage, the velocity of the linear stage, and the angular velocity of the rotational stage for the desired radiation exposure for the material, until data collection is complete.

In another embodiment, a system evaluates material in rotary motion. The system includes a radiation source for generating optical radiation, a detector for detecting fluorescence of the material, a rotational stage for rotating the material in a plane substantially perpendicular to an angle of incidence of the optical radiation on the material, optical components for imaging the optical radiation onto the material and for imaging fluorescence from the material onto the detector, a linear stage for adjusting translation between (a) the rotational stage and (b) the optical components and the detector, and a controller for controlling a rotational angular velocity of the rotational stage and for positioning the linear stage to expose each sample area of the material for a constant quantity of incident optical radiation.

DETAILED DESCRIPTION OF THE EMBODIMENTS

Figure 1:
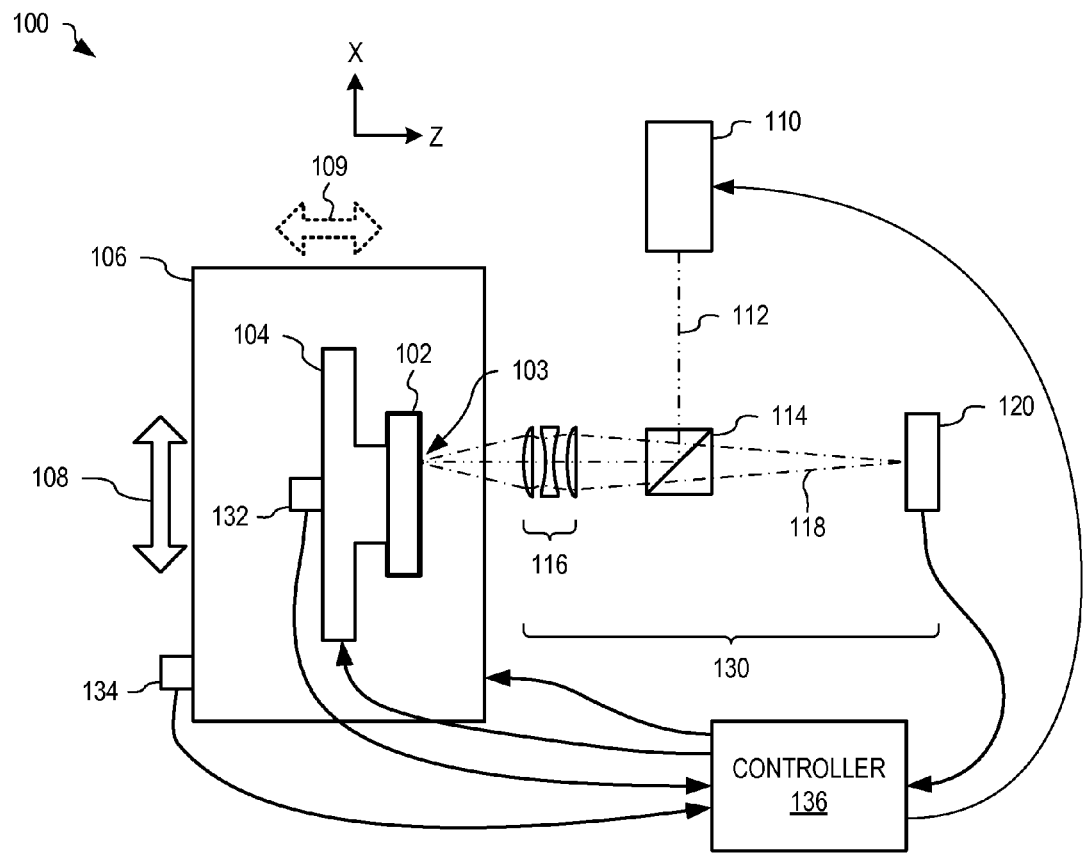
FIG. 1 is a plan elevation of one exemplary system for evaluating a material in rotary motion, in an embodiment.
Figure 2:
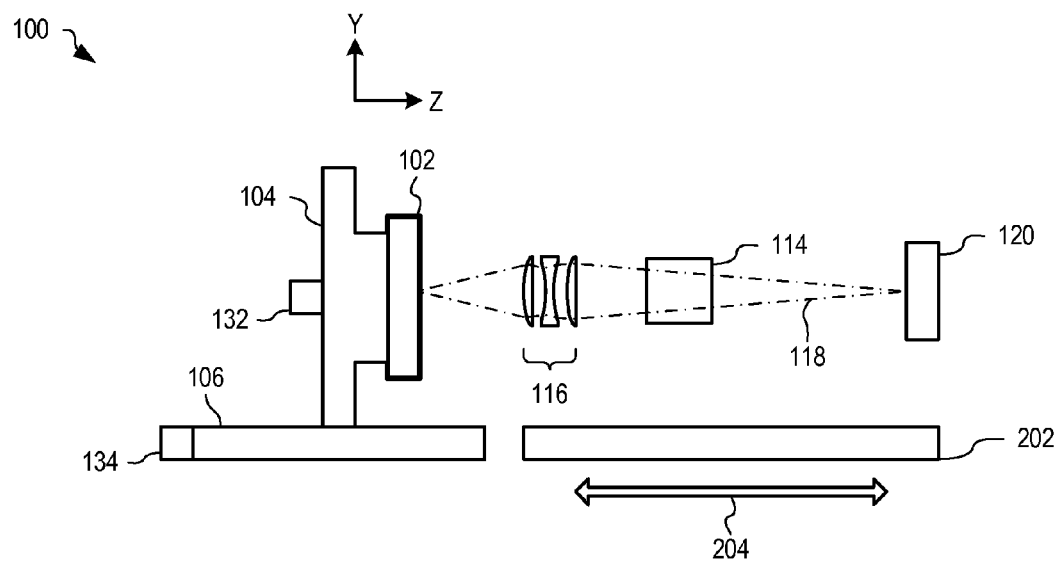
FIG. 2 is a side elevation of the system of FIG. 1.

FIG. 1 is a plan elevation of one exemplary system 100 for evaluating a material 102 in rotary motion. FIG. 2 is a side elevation of the system of FIG. 1. FIGS. 1 and 2 are best viewed together with the following description. Material 102 is mounted on a rotational stage 104, which is in mounted on a single linear stage 106 having linear motion as indicated by arrow 108. A radiation source 110 (e.g., a laser or LED) generates a beam 112 of radiation that is deflected by a beam splitter 114 onto material 102 via an optical group 116. Optical group 116 is illustratively shown with three optical components (e.g., lenses) but may include more or fewer optical components without departing from the scope hereof.

Optical group 116 also functions to image a fluorescent signal 118 from material 102 onto a detector 120. Detector 120 is specifically sensitive to fluorescent signal 118. System 100 is controlled by a controller 136. Controller 136 is for example a computer having a processor and a memory that contains machine readable instructions that, when executed by the processor, control system 100 to evaluate a material 102 in rotary motion as described below.

In one example of operation, optical radiation source 110, beam splitter 114, optical group 116 and detector 120 (collectively shown as components 130) are stationary while (a) rotational stage 104 rotates material 102 to provide rotary movement of material 102 relative to stationary components 130 and (b) linear stage 106 and material 102 move translationally. As material 102 rotates and translates, components 130 deliver radiation to material 102 and collect fluorescent signal 118 at detector 120.

Figure 3:
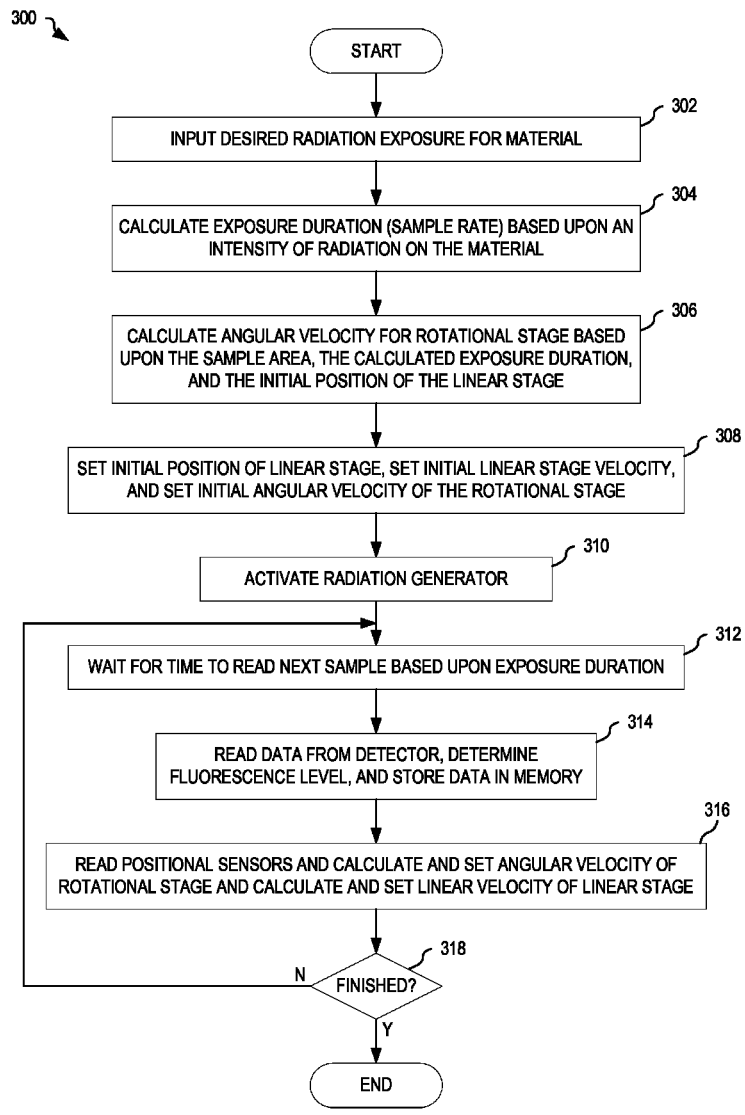
FIG. 3 is a flowchart illustrating one exemplary method for evaluating material in rotary motion, in an embodiment.

FIG. 3 is a flowchart illustrating one exemplary method 300 for evaluating material in rotary motion. Method 300 is for example implemented at least in part within controller 136 of system 100. In step 302, method 300 inputs a desired radiation exposure for a material to be sampled. In one example of step 302, controller 136 is a personal computer and a user inputs a desired radiation exposure for material 102. In step 304, method 300 calculates exposure duration based upon an intensity of incident radiation upon material 102. In one example of step 304, controller 136 calculates exposure duration for sample area 103 based upon intensity of radiation 112 incident thereon.

In step 306, method 300 calculates angular velocity for the rotational stage based upon the sample area, the calculated exposure duration, and the initial position of the linear stage. In one example of step 306, controller 136 calculates angular velocity for rotational stage 104 based upon the area of sample area 103, the calculated exposure duration of step 304, and the initial position of linear stage 106.

In step 308, method 300 sets the initial position of the linear stage, sets the initial linear velocity of the linear stage, and sets the initial angular velocity of the rotational stage. In one example of step 308, controller 136 (a) controls the linear stage to move to an initial position, (b) controls the linear stage to have an initial linear velocity, and (c) controls rotational stage 104 to have the calculated initial angular velocity determined in step 306.

In step 310, method 300 activates the radiation generator. In one example of step 310, controller 136 turns on radiation source 110.

In step 312, method 300 waits for the time to read the next sample based upon the exposure duration. In one example of step 312, controller 136 includes a sample time that is set to the calculated exposure duration, and controller waits until the next sample read time occurs.

In step 314, method 300 reads data from the detector, determines a fluorescence level based upon the data, and stores the determined fluorescence level in memory. In one example of step 314, controller 136 reads data from detector 120, determined a fluorescence level based upon the data read from detector 120, and stores the fluorescence level in a data file within controller 136.

In step 316, method 300 reads positional sensors and calculates angular velocity of rotational stage and calculates linear velocity of linear stage. In one example of step 316, controller 136 calculates a new angular velocity for rotational stage 104 based upon a determined position of linear stage 106, and calculates a new linear velocity for linear stage 106 based upon the determined position of linear stage 106.

Step 318 is a decision. If, in step 318, method 300 determines that all samples have been collected, method 300 terminates; otherwise method 300 continues with step 312 such that steps 312 through 318 repeat until all samples from material 102 have been stored within memory of controller 136. Data stored within controller 136 output for evaluation and/or further processing.

Changes may be made in the above methods and systems without departing from the scope hereof. It should thus be noted that the matter contained in the above description or shown in the accompanying drawings should be interpreted as illustrative and not in a limiting sense. The following claims are intended to cover all generic and specific features described herein, as well as all statements of the scope of the present method and system, which, as a matter of language, might be said to fall therebetween.

What is claimed is:

1. A method for evaluating material in rotary motion, comprising:
    calculating exposure duration based upon an intensity of radiation incident upon a sample area of the material and a desired radiation exposure for the material;
    calculating angular velocity for a rotational stage based upon the sample area, the calculated exposure duration, and an initial position of a linear stage;
    setting the initial position of the linear stage, the initial velocity of the linear stage, and the initial angular velocity of the rotational stage;
    activating a radiation generator and exposing the sample area to radiation;
    waiting for time to read the next sample based upon the calculated exposure duration;
    reading data from the detector, determining a fluorescence level based upon the data, and storing the data in memory;
    reading positional sensors and calculating and setting angular velocity of the rotational stage and calculating and setting linear velocity of the linear stage;
    repeating the steps of waiting, reading data and reading positional sensors until data collection is complete.

2. The method of claim 1, further comprising inputting the desired radiation exposure for the material from a user.

3. A system for evaluating material in rotary motion, comprising:
    a radiation source for generating optical radiation;
    a detector for detecting fluorescence of the material;
    a rotational stage for rotating the material in a plane substantially perpendicular to an angle of incidence of the optical radiation on the material;
    optical components for imaging the optical radiation onto the material and for imaging fluorescence from the material onto the detector;
    a linear stage for adjusting translation between (a) the rotational stage and (b) the optical components and the detector; and
    a controller for controlling a rotational angular velocity of the rotational stage and for positioning the linear stage to expose each sample area of the material for a constant quantity of incident optical radiation.

* * * * *